United States Patent [19]
Rupp

[11] Patent Number: 5,419,773
[45] Date of Patent: May 30, 1995

[54] NON-REUSABLE SYRINGE WITH AUTOMATICALLY ACTIONABLE PROTECTIVE NEEDLE COVER

[76] Inventor: Roberta N. Rupp, 126 Vinal St., Revere, Boston, Mass. 02151

[21] Appl. No.: 204,810

[22] Filed: Mar. 2, 1994

Related U.S. Application Data

[63] Continuation of Ser. No. 946,907, Sep. 18, 1992, abandoned, which is a continuation of Ser. No. 654,251, Feb. 12, 1991, abandoned.

[51] Int. Cl.⁶ ............................................. A61M 5/00
[52] U.S. Cl. .................................. 604/198; 604/192
[58] Field of Search .............. 604/198, 192, 196, 197, 604/263

[56] References Cited

U.S. PATENT DOCUMENTS

| | | | |
|---|---|---|---|
| 4,592,744 | 6/1986 | Jagger et al. | 604/192 |
| 4,631,057 | 12/1986 | Mitchell | 604/198 |
| 4,738,663 | 4/1988 | Bogan | 604/198 |
| 4,762,516 | 8/1988 | Luther et al. | 604/192 |
| 4,804,372 | 2/1989 | Laico et al. | 604/198 |
| 4,816,022 | 3/1989 | Poncy | 604/198 |
| 4,820,277 | 4/1989 | Norelli | 604/192 |
| 4,871,355 | 10/1989 | Kikkawa | 604/198 |
| 4,894,055 | 1/1990 | Sudnak | 604/198 |
| 4,923,447 | 5/1990 | Morgan | 604/198 |
| 4,929,237 | 5/1990 | Medwax | 604/198 |
| 4,943,282 | 7/1990 | Page | 604/198 |
| 4,950,249 | 8/1990 | Jagger et al. | 604/192 |
| 4,966,591 | 10/1990 | Yuen | 604/192 |
| 4,994,044 | 2/1991 | Duca | 604/192 |
| 4,995,869 | 2/1991 | McCarthy | 604/220 |
| 5,026,354 | 6/1991 | Kocses | 604/220 |
| 5,055,102 | 10/1991 | Sitnik | 604/263 |
| 5,057,087 | 10/1991 | Harmon | 604/192 |

*Primary Examiner*—Paul J. Hirsch
*Attorney, Agent, or Firm*—Lorusso & Loud

[57] ABSTRACT

Disclosed is non-reusable syringe with automatically actionable protective needle cover. The invention consists of a syringe which locks the plunger in place after full injection, rendering it unusable. In addition an automatic needle cover is provided which aides as a clamping device and prevents pricking or leaking of a needle. The means of operating the needle cover also allows the needle to be visible for injection.

5 Claims, 8 Drawing Sheets

NON-REUSABLE SYRINGE WITH AUTOMATICALLY ACTIONABLE PROTECTIVE NEEDLE COVER

This is a continuation of application Ser. No. 07/946,907 filed on Sept. 18, 1992, now abandoned which is a continuation of 07/654,251, filed Feb. 12, 1991, now abandoned.

BACKGROUND OF THE INVENTION

1. Field of the Invention

The present invention is in the field of hypodermic syringes used to inject and aspirate liquid material from a patient. More particularly, this invention is directed to render a syringe non-reusable syringe with an engageable retractable cap for the entire needle.

2. Description of the Prior Art

Hypodermic syringes with attached needles are used for the administration of medication and for the withdrawal of material from a patient. These syringes are generally disposable which presents two problems, one is the possible reuse of a syringe and the other and greatest danger is the possibility of being pricked by the needle when handling the syringe. These two concerns are particularly important because the needle and or the syringe may be contaminated and spread disease, such as hepatitis and acquired immune deficiency syndrome (AIDS).

The known non-reusable syringes can easily be reused. In addition often times needles need to be visible for injection. Some devices provide for a shield where the needle is recessed to prevent possible pricking; however, these devices do not provide for a seal directly over the needle whenever the needle is not in use and the neddle is not visible for proper injection. The apparatus of U.S. Pat. No. 4,795,432 to Karczmer does provide a cap at the end of its shield assembly; however, this not only prevents pricking but it also prevent multiple exposure of the needle tip which is sometimes necessary, especially when withdrawing blood for testing. The inventions of U.S. Pat. Nos. 4,507,118 to Dent and 4,767,413 to Haber provide caps but the syringe needle is designed to pass through these caps. Once the needle passes through the caps in these patents, the caps are no longer act as a complete seal to prevent any leakage.

SUMMARY OF THE INVENTION

In light of the above discussed devices, the present invention provides for a less costly syringe that when full injection has been accomplished the syringe is non-reusable. This syringe cannot be easily altered to yield a reusable syringe. In addition, the present invention is provided with a shield assembly that contains a permanent cap, one that easily returns to its sealed position, so that whenever the syringe is not in use not only is the needle shielded but it is also capped. The present invention prevents not only the possibility of pricking but also prevents any possibility of leaking.

Accordingly, it is an object of the present invention to provide a non-reusable syringe.

It is another object of present invention to provide a non-reusable syringe with an engageable retractable cap which reseals the needle and prevents pricking and leaking.

DESCRIPTION OF THE PREFERRED EMBODIMENT

Figure 1:
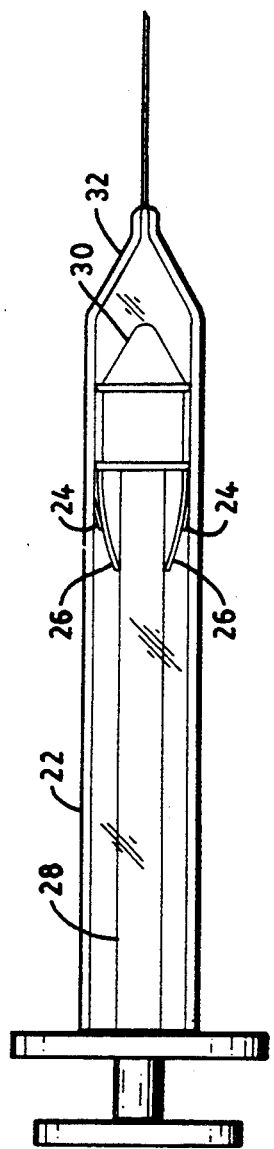
FIG. 1 is a non-reusable disposable syringe before inversion.
Figure 2:
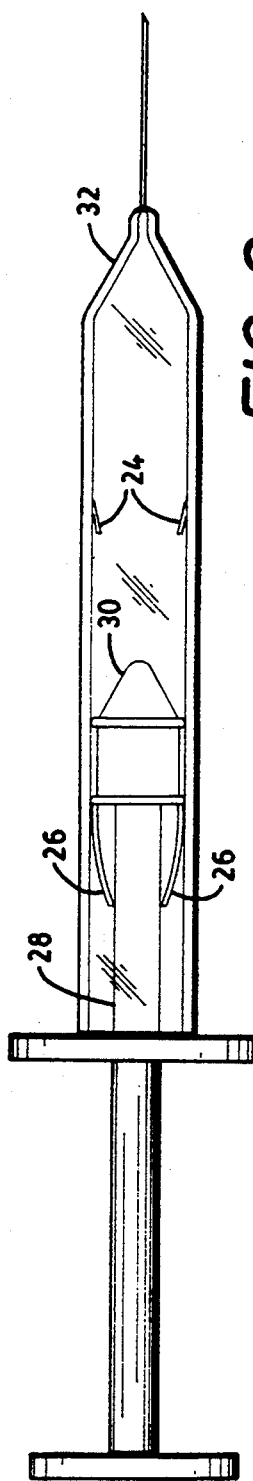
FIG. 2 is a non-reusable disposable syringe during aspiration.

FIGS. 1–4 show an apparatus for injecting into or withdrawing substances from a patient in the form of a hypodermic syringe.

The syringe 20 includes a tubular cylinder 22 with curved brackets 24, near the end of the cylinder. Within the cylinder 22 is the shaft 28 which at one end has a plunger 30 that fits snugly within the head of the syringe 32. The outer rim 26 of the plunger 30 curve inward when aspirating or injecting material, FIGS. 1 and 2. The curved brackets 24 of the cylinder 22 are placed at a greater distance than the fully extended plunger rim 26.

When the plunger 30 is in a fully injected (extended) position, FIG. 3, the head of plunger 30 forces the rim 26 to invert and push outward below the brackets 24 of the cylinder 22.

Figure 3:
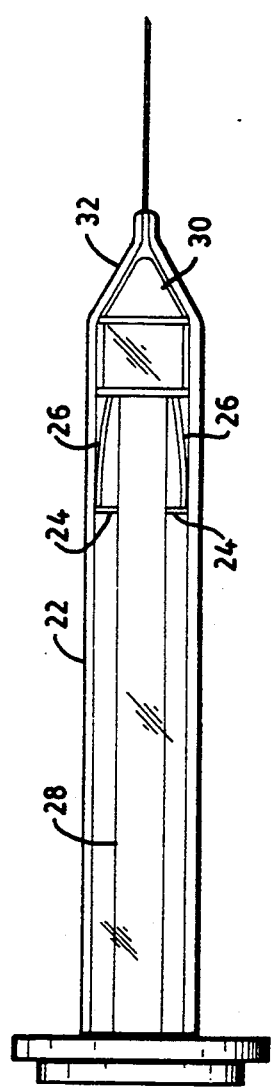
FIG. 3 is a non-reusable disposable syringe fully extended.

The shaft 28 and plunger 30 in FIG. 3 are now locked into position. The preferred embodiment is to have the brackets 24 and rim 26 made of metal, the advantage being that is is difficult to remove or file down. In addition, the preferred material of the plunger 30 is rubber. Removal of the metal rim 26 from the rubber plunger 30 would leave holes in the rubber plunger 30 and thereby rendering the syringe useless.

Figure 4:
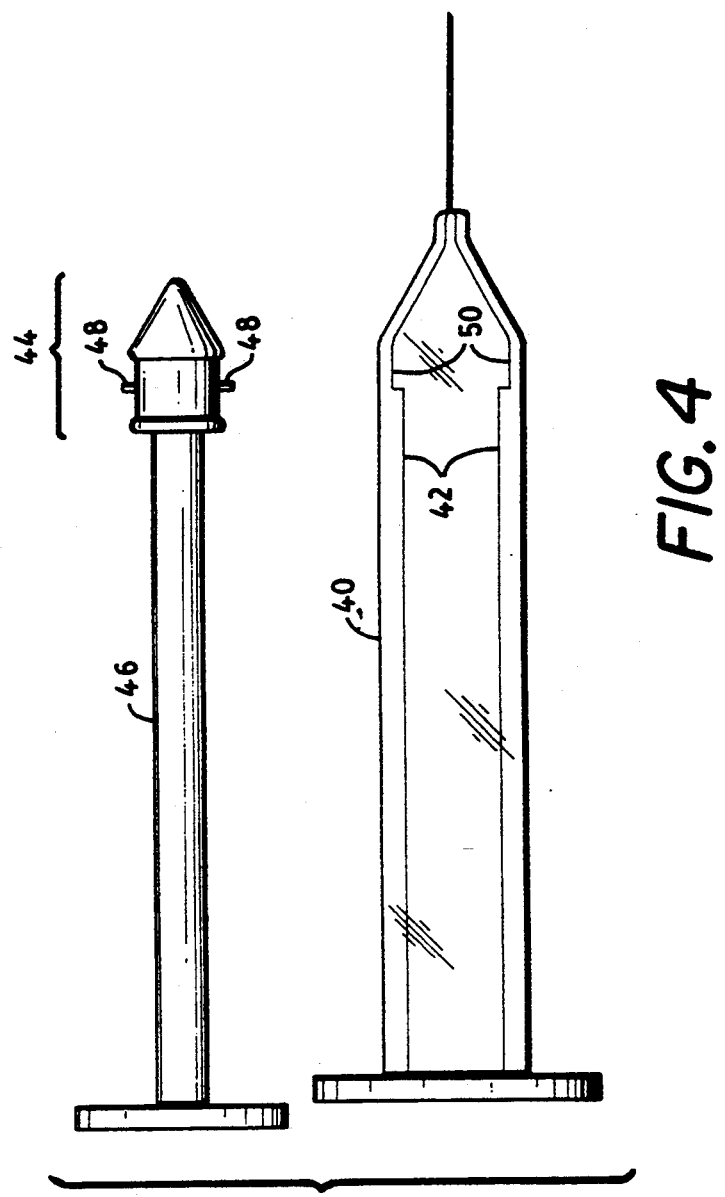
FIG. 4 is a non-resusable disposable syringe assembly.

A second embodiment, FIG. 4 shows the shaft 46 with a curved rubber plunger 44 and a locking spring 48 through the rubber plunger 44. The rubber plunger 44 fits snugly within the cylinder 40. The locking spring 48 is not at it's fully extended position when the plunger 44 is located above the depressions 42 of the cylinder 40.

The cylinder 40 has internal depressions 42 which run along the cylinder with its deepest point of depression near the end of the cylinder 40. The depressed area 50 must be slightly greater than the distance between the plunger 44 head and the locking spring 48 which is located in the middle of the plunger 44.

When the plunger is fully extended, beyond the internal depressions 42, the locking springs 48 push toward the wall of the cylinder 40 in the depressed area 50. The extended springs 48 prevent the plunger 46 from being pulled from the fully extended position.

Like the metal rim 26 of FIG. 3, removal of the locking springs 48 would damage the rubber plunger 44 and make it impossible to retain fluid in the syringe.

Figure 5:
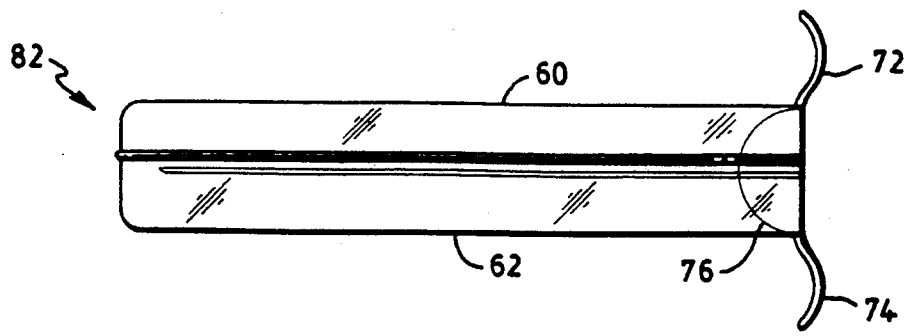
FIG. 5 is a protective needle cap.
Figure 6:
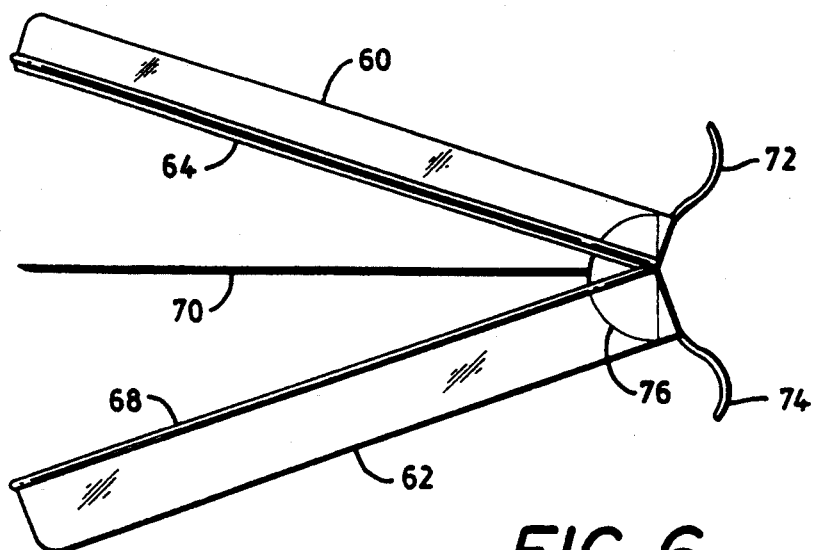
FIG. 6 is a opened protective needle cap.
Figure 7:
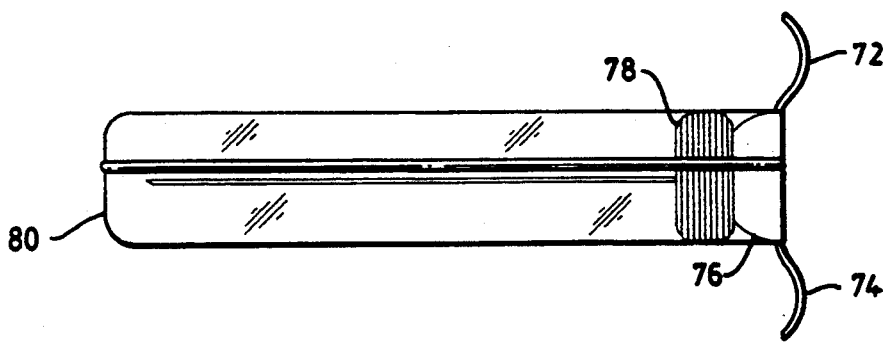
FIG. 7 is a clamped protective needle cap.

In order that a non-reusable syringe may not be a threat to society, the needle of the syringe must likewise be rendered safe. FIGS. 5-7 show the preferred embodiments of a non-removable cap for a needle. The cap may be attached to a needle that is permanently affixed to a syringe or it may be attached separately.

The preferred material used for the cap 82 is a rigid, clear plastic. The cap consists of two half cylinders 60 and 62. Each half cylinder having either a rubber male 64 or female 66 fitting to assure a tight closure around a sterile needle 70. On each end of the cylinder halves 60 and 62 are extension tabs 72 and 74.

At the base of the needle 70 the preferred embodiment is a rubber lower seal 76 to ensure fit with rubber ports of medication 78.

Pressure is exerted on the tabs 72 and 74 which forces the cylinder halves 60 and 64 to open exposing the needle 70, FIG 6. Releasing the pressure from extension tabs 72 and 74 automatically reseals the cap 82, FIG. 7.

The advantage of the above described embodiment in FIG. 7, is that when medication is being administered for a period of time, the pressure is released from the extension tabs 72 and 74 and the half cylinders 60 and 62 of the cap act as a clamp which ensures that the needle will not easily slip out of position and even if it should the cap would automatically close over the end of the needle 70 and the needle 70 would not be a threat to anyone in the vicinity.

Figure 7A:
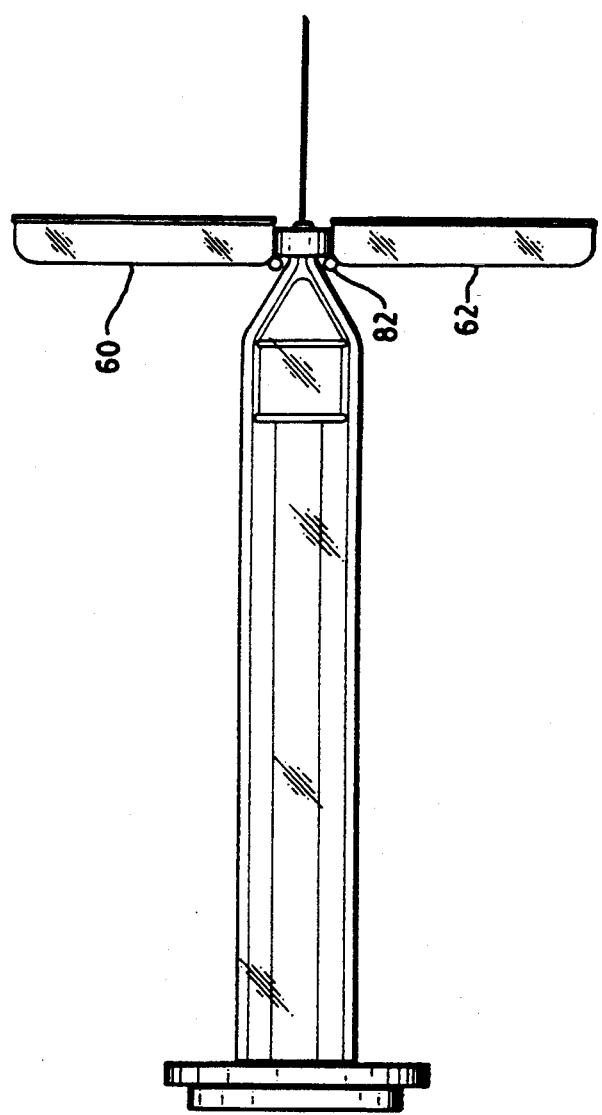

Another variation of FIGS. 5-7 would be to have a spring device 82 as seen in FIG. 7a rather than the extension tabs 72 and 74. Pressure can be exerted on the spring devices 82 which would force the cylinders 60 and 62 to open. The spring devices 82 can be locked in place so that the needle is fully visible for injection or may be relased once the needle is positioned on tubing so as to form a clamp.

Figure 8:
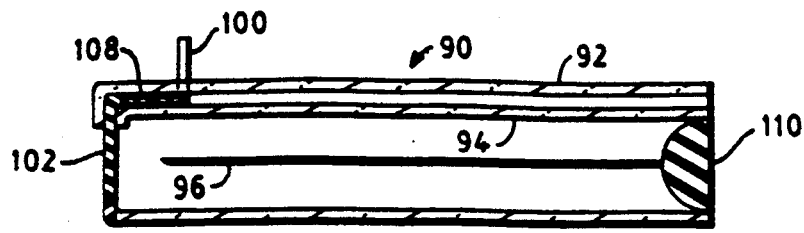
FIG. 8 is a retractable protective needle cap.
Figure 9:
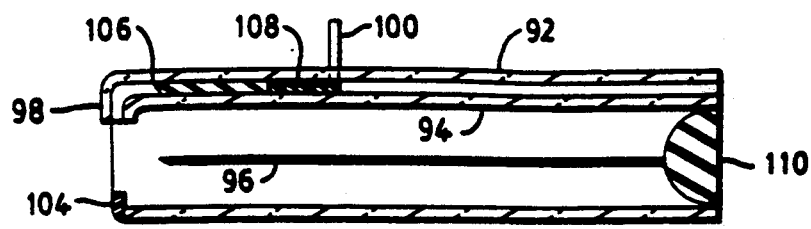
FIG. 9 is a retracted protective needle cap.
Figure 10:
FIG. 10 is a retracted protective needle cap in a clamp position.

FIGS. 8-10 illustrates a variation of the needle protector cap assembly (cap and shield assembly) with a preferred embodiment that is made of a rigid cylinder 90 of clear plastic with an inner 92 and outer 94 wall that extends beyond the needle tip 96. The outer wall 94 extends slightly beyond and around the inner wall 92, forming a lip 98 over the inner wall 92, FIG. 9. The outer wall also has a opening (not shown) that runs partially along the side of the shield to allow a lever 100 to be pushed down alongside.

The cap 102 of the preferred shield assembly is made of rubber. The cap 102 as can be seen in FIG. 9 is in two sections 104 and 106. Each section has either a rubber male or female fitting to assure a tight closure around a sterile needle. One cap section 104 is firmly affixed to the end of the cylinder 90. The other section 106 is attached to the lever 100 through tension means 108. When the lever 100 is pushed towards the base 110 of the needle 96 the cap section 100 easily slides between the outer 94 and the inner 92 wall.

When the lever 100 is released the retracted cap section 100 returns to its closed position FIG. 10. The lip 98 allows the cap 100 to return to its proper closed position. The advantages of such an embodiment is that the needle is always in a recessed position so that injury as the result of pricking can be avoided, when pressure is released from the lever 100 the needle is either resealed or when medication is being administered the cap acts as a clamp which ensures that the needle will not easily slip out of position during administration. This embodiment is also advantageous for Y ports or for Heparin locks.

Figure 11:
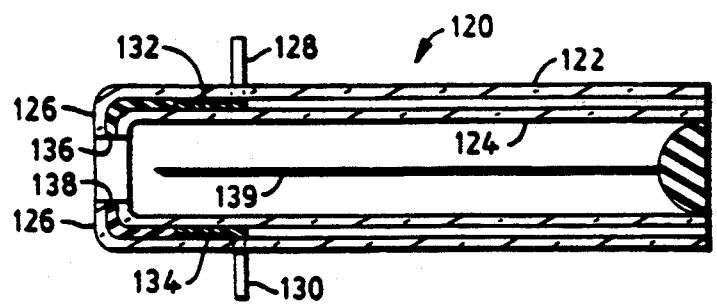
FIG. 11 is a dual retractable protective needle cap.

A shield assembly in which both sections of the cap 136 and 138 are retractable is demonstrated in FIG. 11. In this embodiment the shield assembly 120 is defined by a double walled thickness cylinder. The outer wall 122 extends beyond and over the inner wall 124 forming a lip 126. The sharp end of the needle 139 is recessed within the cylinder 120. On opposite sides of the cylinder there are two tracks (not shown) cut out of the outer wall 122 to allow the levers 128 and 130 to slide alongside the cylinder 120.

Each cap section 136 and 138 is attached to tension means 132 and 134 which is attached to corresponding lever 128 and 130. When pressure is exerted upon the levers 128 and 130 the cap sections 136 and 138 pull back between the inner 124 and outer walls 122 of the cylinder. Upon releasing the levers 128 and 130, the cap sections 136 and 138 automatically return to the sealed position.

The advantage of both cap sections 136 and 138 being retractable is that a more uniform clamp can be attained when administrating medications.

Figure 12:
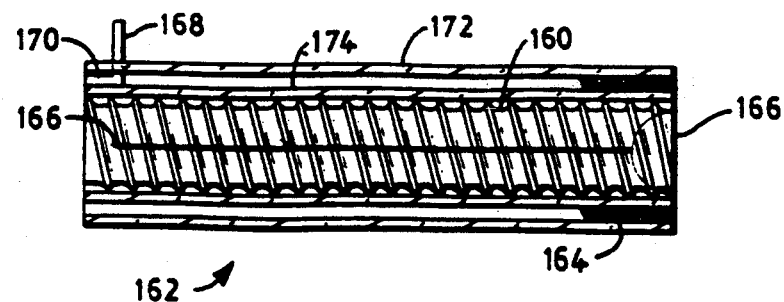
FIG. 12 is a retractable protective needle cap.
Figure 13:
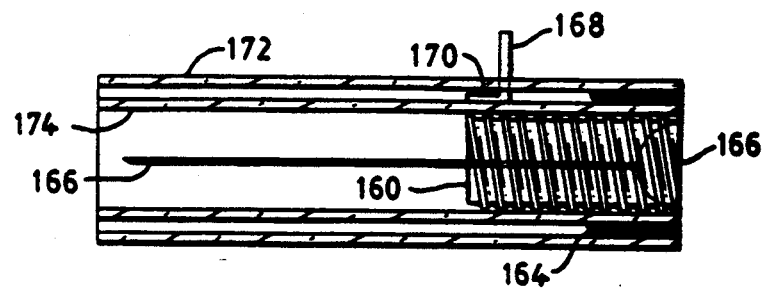
FIG. 13 is a retracted protective needle cap.

Another for a retractable cap as described above can be seen in FIGS. 12 and 13. This embodiment has the permanent cap consisting of either one or two sides of corrugate-like tubing 160 that is joined to the lever 168 through tension means 170. The lever 168 slides between the outer 172 and the inner 174 wall of the cylinder 162. The cylinder 162 is affixed to the syringe and is made of clear plastic. At the base of the needle 166 there is a spring apparatus 164. The spring apparatus 164 is nesseccary to create a firm pressure seal around a port to prevent pulling our to needle. When the lever 168 is pulled back, the corrugated-like tubing 160 folds back and exposes the needle 166 for insertion, FIG. 13. When the lever 168 is released the corrugated tubing 160 springs back and forms a seal around the needle 166 port, FIG. 12. A dual retractable cap as described above can be similarly employed.

Figure 14:
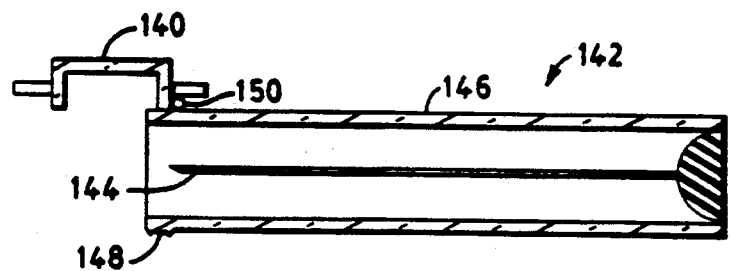
FIG. 14 is a removable protective needle cap.

The permanent cap illustrated in FIG. 14 is a cap 140 that can be hinged 150 onto the cylinder 142. When the needle 144 is to be used the cap 140 can be released from the cylinder while it is still attached on one side 150 of the cylinder 140. While the needle 144 is in use the cap 140 can be fastened alongside the cylinder 146. When through with the needle 144 the cap 140 can be released and fastened at its closed position 148.

There are instances where the length of the needle must be exposed for use, such as when medication is being administered directly into a patient or body fluid is being withdrawn. This being the case a shield assembly is necessary that retracts entirely along the length of the needle.

Figure 15:
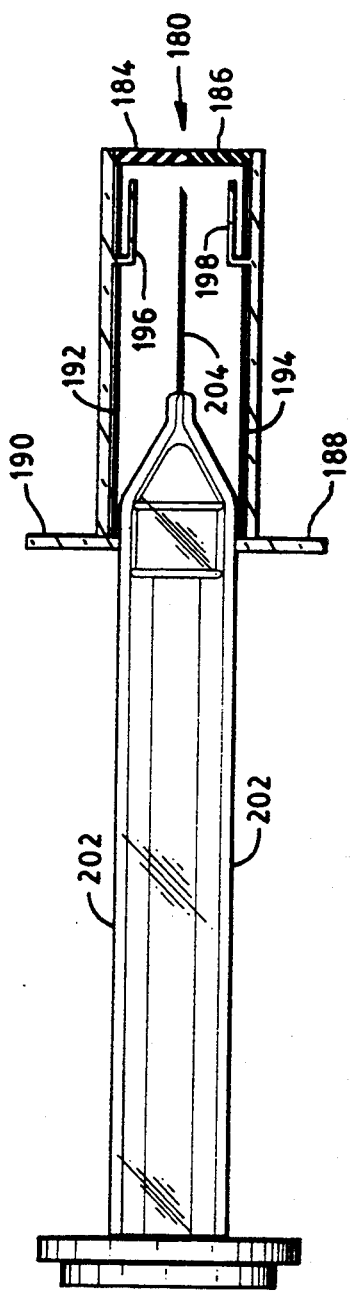
FIG. 15 is a retractable needle cap and shield assembly.
Figure 16:
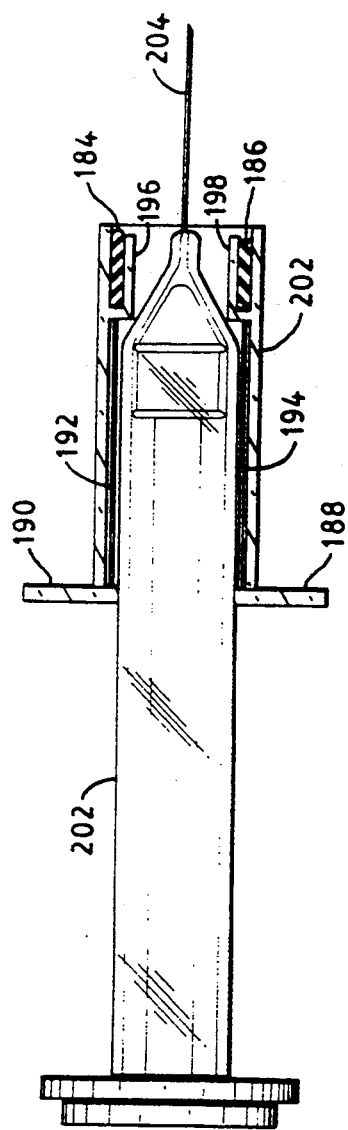
FIG. 16 is a retracted needle cap and shield assembly.

A retractable cap and shield assembly is demonstrated in FIGS. 15 and 16. The cap 180 is made of a rubber substance and the sides of the assembly (cylinder) 182 is made of a more clear durable plastic. The cap sections 184 and 186 have a rubber male—female fitting and are attached to the levers 188 and 190 through tension means 192 and 194. As the cap sections 184 and 186 are pulled back they retract into compartments 196 and 198 along the outer wall 200 of the assembly on either side of the needle 204. Once the cap sections 184 and 186 are in the in the compartments 196 and 198, additional pressure of the tension means 192 and 194 causes the outer wall 200 of the durable plastic assembly to retract over the inner wall 202 of the assembly, thereby exposing the needle 204, FIG. 16. When the needle 204 is exposed, the levers 188 and 190 can be locked in place in grooves 206 and 208 along the side of the inner wall 202 of the assembly. When the levers 188 and 190 are released the assembly automatically reseals over the needle 204, FIG. 15.

Figure 17:
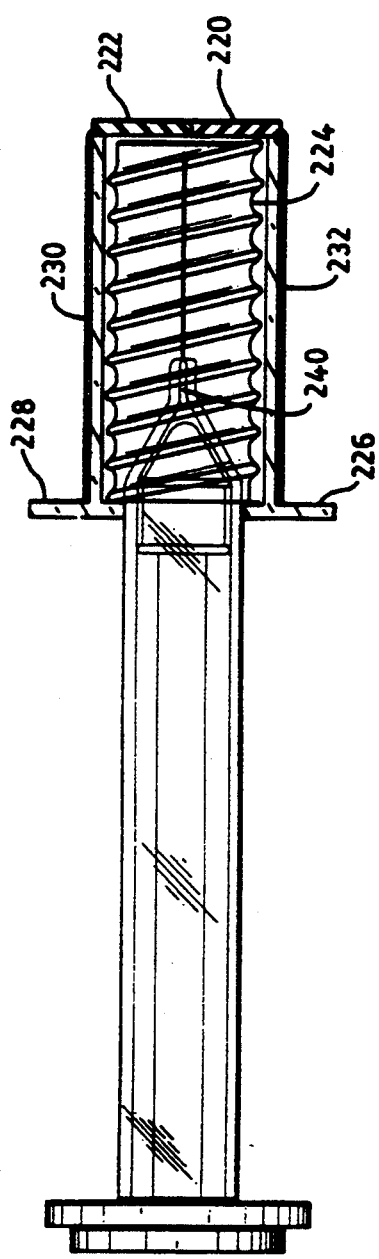
FIG. 17 is a retractable needle cap and shield assembly.
Figure 18:
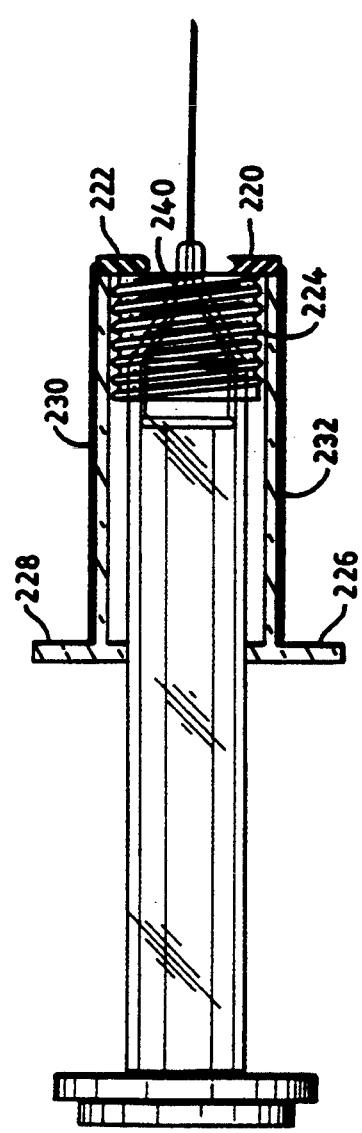
FIG. 18 is a retracted needle cap and shield assembly.

Another variation of the above described shield assembly is seen in FIGS. 17 and 18. The cap sections 220 and 222 are made of rubber and are attached to corrugated-like tubing 224 which is attached to levers 226 and 228 through tension means 230 and 232. When pressure is applied to the levers 226 and 228 the rubber cap sections 220 and 222 are retracted until they are stopped against the wall of the corrugated-like tubing 224, FIG. 17. Additional pressure on the levers 226 and 228 causes the corrugated-like tubing 224 to fold back at the base of the needle 240, FIG. 18. Once the desired needle 240 exposure is attained the levers 226 and 228 can be secured in the grooves 234 and 236 along the clear plastic wall 238 of the assembly. When the levers 226 and 228 are released the assembly automatically reseals over the needle 240, FIG. 17.

While the foregoing invention has been described with references to its preferred embodiments, it should not be limited to such embodiments since various alterations and modifications will occur to those skilled in the art. For example, the plastic and rubber materials used could be replaced by equally effective materials. All such variations and modifications are intended to fall within the scope of the appended claims.

What is claimed:

1. A method for administering a substance to a patient via a hypodermic needle comprising the steps of:
    providing a hypodermic needle having a cap comprising a tubular member encircling said hypodermic needle, said tubular member terminating in a perpendicular top surface formed by a plurality of cap sections, which when said hypodermic needle is in an unused position, respectively extend over to completely cover a sharp end of said hypodermic needle to prevent pricking, said plurality of cap sections, when said hypodermic needle is in a used position, being retractable towards said tubular member, thereby creating an opening which uncovers said sharp end of said hypodermic needle,
    providing a biasing means which biases said plurality of cap sections in the unused position to cover said hypodermic needle to prevent pricking;
    administering the substance through the needle by exerting a force on said plurality of cap sections against said biasing means, to retract said plurality of cap sections towards said tubular member, thereby exposing said hypodermic needle;
    utilizing the hypodermic needle;
    releasing the force against said plurality of cap sections to allow said plurality of cap sections to extend to their unused positions, respectively, thereby covering said sharp end of said hypodermic needle to prevent pricking.

2. The method according to claim 1, wherein said biasing means is corrugated tubing.

3. The method according to claim 1, said step of administering the substance further comprising retracting said plurality of cap sections along a plane perpendicular to said tubular member.

4. The method according to claim 1, said step of providing a biasing means further comprising providing a plurality of tension members coupled with said plurality of cap sections, respectively, for biasing said plurality of cap sections.

5. The method according to claim 1, said step of administering the substance further comprising retracting said plurality of cap sections, thereby causing displacement of said plurality of cap sections from a plane perpendicular to the plane of said tubular member, to a plane parallel to the plane of said tubular member.

* * * * *

UNITED STATES PATENT AND TRADEMARK OFFICE
CERTIFICATE OF CORRECTION

PATENT NO. : 5,419,773
DATED : May 30, 1995
INVENTOR(S) : Rupp

It is certified that error appears in the above-indentified patent and that said Letters Patent is hereby corrected as shown below:

Column 1, Line 35: Delete "neddle" and insert --needle--;

Column 1, Line 38: Delete "prevent" and insert --prevents--;

Column 1, Line 44: Delete "are";

Column 1, Line 61: Insert --the-- after "of";

Column 1, Line 66: Delete "DRAWING" and insert --DRAWINGS--;

Column 2, Line 34: Delete "curve" and insert --curves--;

Column 2, Line 46: Delete "is" (first occurrence) and insert --it--;

Column 2, Line 49: Delete "and";

Column 2, Line 55: Delete "it's" and insert --its--;

Column 2, Line 67: Delete "46" and insert --44--;

Column 3, Line 13: Delete "66" and insert --68--;

Column 3, Line 20: Delete "64" and insert --62--;

Column 3, Line 40: Delete "illustrates" and insert --illustrate--;

Column 3, Line 43: Delete "92" and insert --94-- therein; delete "94" and insert --92-- therein;

UNITED STATES PATENT AND TRADEMARK OFFICE
CERTIFICATE OF CORRECTION

PATENT NO. : 5,419,773
DATED : May 30, 1995
INVENTOR(S) : Rupp

It is certified that error appears in the above-indentified patent and that said Letters Patent is hereby corrected as shown below:

Column 3, Line 44: Delete "94" and insert --92--;

Column 3, Line 45: Delete "92" and insert --94--;

Column 3, Line 46: Delete "92" and insert --94--;

Column 3, Line 47: Delete "a" and insert --an--;

Column 3, Line 58: Delete "100" and insert --106--;

Column 3, Line 59: Delete "94" and insert --92-- therein; delete "92" and insert --94-- therein;

Column 3, Line 61: Delete "100" and insert --106--;

Column 3, Line 62: Delete "100" and insert --102--;

Column 3, Line 63: Delete "is" and insert --are--;

Column 4, Line 15: Delete "is" and insert --are--;

Column 4, Line 16: Delete "lever" and insert --levers--;

Column 4, Line 25: After "Another" insert --embodiment--;

Column 4, Line 34: Delete "nesseccary" and insert --necessary--;

Column 4, Line 35: Delete "our to" and insert --out the--;

UNITED STATES PATENT AND TRADEMARK OFFICE
CERTIFICATE OF CORRECTION

PATENT NO. : 5,419,773
DATED : May 30, 1995
INVENTOR(S) : Rupp

It is certified that error appears in the above-indentified patent and that said Letters Patent is hereby corrected as shown below:

Column 4, Line 46: Delete "140" and insert --142--;

Column 4, Line 47: After "cylinder" insert --shaft--;
Column 4, Line 64: Delete "200" and insert --202--;
Column 4, Line 66: Delete "in the" (second occurrence);
Column 4, Line 68: Delete "200" and insert --202--;
Column 5, Line 1: Delete "202";

Column 5, Line 5: Delete "202"; and

Column 6, Line 33: Delete "1" and insert --4-- therefor.

Signed and Sealed this

Seventh Day of November, 1995

Attest:

Attesting Officer

BRUCE LEHMAN

Commissioner of Patents and Trademarks